United States Patent [19]

Sugiyama et al.

[11] Patent Number: 4,855,415
[45] Date of Patent: Aug. 8, 1989

[54] GLUCOSYLMORANOLINE DERIVATIVES

[75] Inventors: Makoto Sugiyama, Kyoto; Yoji Ezure, Otsu; Yoshiaki Yoshikuni, Uji; Yukio Fujita, Takatsuki, all of Japan

[73] Assignee: Nippon Shinyaku Co., Ltd., Japan

[21] Appl. No.: 91,822

[22] Filed: Sep. 1, 1987

[30] Foreign Application Priority Data

Sep. 2, 1986 [JP] Japan .................................. 61-207450

[51] Int. Cl.$^4$ .................. C07H 17/02; C07D 401/12; A61K 31/10; A61K 31/445
[52] U.S. Cl. .................................. 536/17.4; 536/17.9; 514/866
[58] Field of Search ................ 536/17.4, 17.9; 514/25, 514/866

[56] References Cited

U.S. PATENT DOCUMENTS

| | | |
|---|---|---|
| 4,338,433 | 7/1982 | Matsumura et al. .................. 536/46 |
| 4,363,802 | 12/1982 | Matsumura et al. ................ 536/17.4 |
| 4,533,668 | 8/1985 | Matsumura et al. ................. 514/321 |

FOREIGN PATENT DOCUMENTS

| | | | |
|---|---|---|---|
| 2064527 | of 1981 | United Kingdom . | |
| 2067989 | 8/1981 | United Kingdom | 514/866 |
| 2067990 | 8/1981 | United Kingdom | 514/866 |
| 2181729 | of 1987 | United Kingdom . | |

Primary Examiner—Ronald W. Griffin
Assistant Examiner—Nancy S. Carson
Attorney, Agent, or Firm—Jacobs & Jacobs

[57] ABSTRACT

A compound of formula (I)

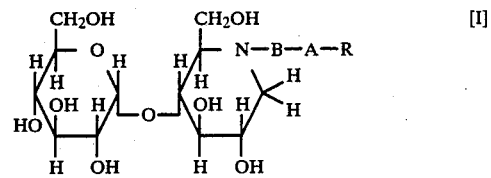

wherein:
B is a divalent substituted or unsubstituted, cyclic or acyclic, saturated or unsaturated hydrocarbon group;

A is a linking group selected from the group consisting of —O—, —S—, —N(H)—, —N(R)—, —C(O)— and combinations of two or more thereof or A is a direct bond; and R is a monovalent substituted or unsubstituted, cyclic or acyclic, saturated or unsaturated hydrocarbon group, a monovalent substituted or unsubstituted aromatic hydrocarbon group, or a monovalent substituted or unsubstituted heterocyclyl provided that B—A—R may not represent hydrogen, lower alkyl, or a monovalent cyclic or acyclic hydrocarbon group having one or more hydroxyl groups, which is useful for inhibiting an increase in blood glucose in humans and for the treatment of diabetes mellitus.

23 Claims, No Drawings

GLUCOSYLMORANOLINE DERIVATIVES

The present invention relates to compounds of formula (I), which inhibit blood glucose increase in animals:

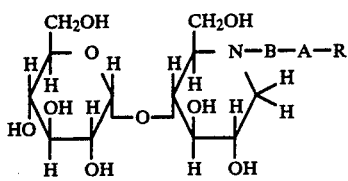

wherein:

B is a divalent substituted or unsubstituted, cyclic or acyclic, saturated or unsaturated hydrocarbon group;

A is a linking group selected from the group consisting of —O—, —S—, —N(H)—, —N(R)—, —C(O)— and combinations of two or more thereof or A is a direct bond; and R is a monovalent substituted or unsubstituted, cyclic or acyclic, saturated or unsaturated hydrocarbon group, a monovalent substituted or unsubstituted aromatic hydrocarbon group, or a monovalent substituted or unsubstituted heterocyclyl provided that B—A—R may not represent hydrogen, lower alkyl, or a monovalent cyclic or acyclic hydrocarbon group having one or more hydroxyl groups.

Moranoline has the following chemical structure and is useful in the treatment of diabetes mellitus:

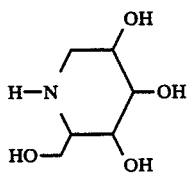

Moranoline was first isolated from mulberry bark, (cf. Yagi, et al: Nippon Nogei Kagaku Kaishi, vol. 50, page 571, 1976; Japanese Laid Open Publication 52/83951), and was later manufactured by fermentation using a microorganism belonging to the genus Streptomyces. (cf. Japanese Laid Open 54/84094).

Compounds (I) wherein B—A—R is hydrogen or lower alkyl are disclosed in Japanese Laid Open Application 2297/82 and others, and compounds (I) wherein B—A—R is a hydrocarbon group substituted by one or more hydroxyl are disclosed in Japanese Patent Application 227601/85. Compounds (I) wherein B—A—R is alkyl substituted by one or more hydroxyl are also disclosed in Sugiyama et al U.S. patent application Ser No. 917,739, filed Oct. 10, 1986 which is incorporated herein by reference thereto.

The characteristic feature of the compounds (I) of the present invention is that they have N-substituted glucosylmoranoline as the fundamental skeleton and a specified substituent, B—A—R, at the nitrogen atom.

As used herein, the term hydrocarbon group for B and R includes a hydrocarbon group containing any desired number of carbon atoms, and includes cyclic or acyclic hydrocarbon or both, such as aliphatic, cycloaliphatic, aliphatic-cycloaliphatic or cycloaliphatic-aliphatic and the like. Suitably, the hydrocarbon group may contain from about 1 to about 15 carbon atoms, such as alkylene of from about 1 to about 15 carbon atoms, alkenylyl or alkynylyl of from about 2 to about 15 carbon atoms, or cycloalkylene, cycloalkenylyl or cycloalkynylyl of from about 3 to about 10 carbon atoms, preferably from about 3 to about 7 carbon atoms, and the like. In a preferred embodiment of the invention, B is alkylene of from about 1 to about 6 carbon atoms or alkenylyl or alkynylyl of from about 2 to about 6 carbon atoms.

If desired, the hydrocarbon group for B and R may be unsubstituted or substituted by one or more substituents, such as halogen, hydroxyl, mercapto, amino, aryl, substituted aryl, heterocyclyl and substituted heterocyclyl. As used herein, the term aryl includes mono- and polycyclic aryl and the term heterocyclyl includes aliphatic and aromatic heterocyclyl of from about 5 to about 12 ring members, containing 1, 2 or 3 heteroatoms, which may be the same or different, selected from the group consisting of nitrogen, oxygen and sulfur. The terms substituted aryl and substituted heterocyclyl as used herein are aryl and heterocyclyl substituted by one or more monovalent hydrocarbon (as defined above), halogen, hydroxy, mercapto, amino, carboxyl, alkoxycarbonyl, aryl and heterocyclyl. Examples of aryl include phenyl, naphthyl and the like. Examples of heterocyclyl include pyridyl, morpholinyl, thienyl, piperidyl, benzimidazolyl and the like. The term alkoxycarbonyl includes alkoxycarbonyl of from about 1 to 15 carbon atoms in the alkoxy moiety, preferably from about 1 to about 6 carbon atoms.

The linking group A is a direct bond or is —O—, —S—, —N(H)—, —N(R)— (R is as defined above), —C(O)— or a combination of two or more of these groups. Preferably A is a direct bond, —C(O)—, —O— or —N(R)—.

As stated above, R may be a monovalent hydrocarbon, aromatic hydrocarbon or heterocyclic group, these terms being defined above. Preferably, R is alkyl of from about 1 to about 6 carbon atoms, alkenyl of from about 2 to about 6 carbon atoms, phenyl or phenyl substituted by alkyl of from about 1 to about 6 carbon atoms, halogen, hydroxy, carboxyl or alkoxycarbonyl of from about 1 to 6 carbon atoms in the alkoxy moiety. Most preferably, R is alkyl of from about 1 to about 6 carbon atoms, alkenyl of 2 to 6 carbon atoms or phenyl.

In a presently preferred embodiment of the invention, A is a direct bond and B is alkenylyl of from about 2 to about 6 carbon atoms and R is alkyl of from about 1 to about 6 carbon atoms, or B is alkylene of from about 1 to about 6 carbon atoms and R is alkenyl of from about 2 to about 6 carbon atoms.

In another presently preferred embodiment of the invention, B is alkylene of from about 1 to about 6 carbon atoms, A is —O— and R is phenyl.

The compounds (I) of the present invention are basic, and, accordingly, they may form salts with acids. When such salts are pharmaceutically acceptable, they are, of course, useful in the present invention.

Compounds (I) of the present invention can be prepared by reacting by reaction 4-O-alpha-D-glucopyranosyl-moranoline with a halide X—B—A—R, wherein X is halogen, preferably chlorine or bromine, and B, A, and R are as defined above, in a suitable solvent, such as dimethyl sulfoxide and dimethyl formamide, in the presence of an acid removing agent, such as alkali metal carbonates and bicarbonates, in analogy to conventional methods for alkylating amines.

When desired the nitrogen atom of 4-O-alpha-D-glucopyranosyl-moranoline can be protected in a conventional manner such as, for example, by the use of benzyloxycarbonyl chloride or a similar reagent. Thus, 4-O-alpha-D-glucopyranosyl- moranoline may be dissolved in 10 to 20 times by volume of N,N- dimethyl formamide or dimethyl sulfoxide at 50° to 70° C. with stirring. The solution is then allowed to stand to cool to room temperature, two to three moles of benzyloxycarbonyl chloride is added in the presence of two to three moles of anhydrous potassium carbonate or anhydrous sodium carbonate per mole of 4-O-alpha-D-glucopyranosyl-moranoline, the mixture is stirred for 3 to 5 hours at room temperature, the solvent is evaporated in vacuo, the residue is washed with 1 to 3 times by volume of ether or chloroform, then 5 times by volume of water is added and the mixture is desalted by passing through 50 times the amount of Sephadex LH-20, which is swollen with a 1:1 mixture of water and methanol, and the desired N-protected compound is obtained in pure state.

The protection of the hydroxyl group may also be conducted in a conventional manner. Thus, the above-obtained N-protected compound may be dissolved in 10 times the amount of anhydrous pyridine at room temperature, an 8 to 10 times molar amount of benzyl chloride is added, the mixture is stirred for 5 to 24 hours when stirring, the solvent is evaporated therefrom in vacuo, the residue is washed with n-hexane, and then dissolved in 10 times the amount of water. The solution is extracted with twice the amount of ethyl acetate for 2 to 5 times repeatedly, the extracts are combined, dried with a drier, such as anhydrous sodium sulfate or magnesium sulfate, filtered to remove the drier, and ethyl acetate is evaporated therefrom in vacuo to give N- and O-protected 4-O-alpha-D-glucopyranosylmoranoline.

The removal or detachment of the protective group of such protected compounds may also be conducted in a conventional manner. For example, the N- and O-protected compound is dissolved in 5 to 10 times the amount of solvent (e.g. chloroform or ether) and stirred for 5 to 10 hours at room temperature together with a 2 to 5 times molar amount of trifluoroacetic acid, whereupon the N-protective group can be easily removed. For further purification, the reaction solution is made alkaline with, for example, 10% aqueous solution of sodium carbonate, stirred, then allowed to stand, the chloroform layer is washed with water, dried with anhydrous magnesium sulfate or sodium sulfate, and chloroform is evaporated therefrom in vacuo to give the O-heptabenzyl derivative of 4-O-alpha-D-glucopyranosyl- moranoline.

The conversion of the secondary nitrogen to a tertiary nitrogen atom of the resulting O-heptabenzyl derivative can be conducted as given in the examples. For example, the reaction thereof with beta-bromoethanol gives the N-2-hydroxyethyl compound, which is also useful as an intermediate for the manufacture of various analogous compounds.

For instance, a halogenated derivative may be prepared as follows. Thus, the N-2-hydroxyethyl compound is treated, as mentioned in Examples 23 and 24, with a 2 to 5 times molar amount of a halogenating agent (e.g. thionyl chloride, phosphorus oxychloride, phosphorus tribromide, etc.) in the presence of 10 times the amount of chloroform or it may be treated with a large excess (e.g. 20 to 30 times) of the above halogenating agent in the absence of a solvent followed by refluxing for 3 to 5 hours to give the desired halogenated derivative. The resulting halogenated derivative may be used, without purification, for the succeeding reactions if desired.

For example, the introduction of a dialkylamino group is conducted as follows. Thus, a chlorinated compound is heated for several hours with 1 to 2 eqivalents of a dialkylamine in 10 to 20 times the amount of an inert solvent (e.g. tetrahydrofuran, dioxane, ether, etc.) in the presence of 1 to 2 equivalents of an acid remover (e.g. triethylamine, N,N-dimethylaniline, etc.).

For another example, the introduction of an alkoxyalkyl group is conducted as follows. Thus, a chlorinated compound is made to react with sodium ethylate at 40°–70° C. for 3 to 6 hours in 50 to 100 times the amount of ethanol, then the solvent is evaporated therefrom, and the residue is treated with Dowex 50W×2 ($H^+$) to give the purified N-2-ethoxyethyl compound.

Debenzylation of the O-heptabenzyl N-substituted 4-O-alpha-D-glucopyranosyl-moranoline prepared in the above manner is also carried out in a conventional manner. Thus, 1/100 to 1/10 times by weight of palladium-carbon is added thereto in 10 to 30 times the amount of an alcoholic solvent (e.g. methanol or ethanol) or an ester type solvent (e.g. ethyl acetate) and hydrogenation is conducted under ordinary pressure until no more hydrogen is absorbed, followed by removal of the catalyst and evaporation of the solvent to give the desired debenzylated material. The product may be purified by, for example, passing an aqueous solution thereof through 10 to 50 times the amount of Dowex 50W×2 ($H^+$), washing the column with water until the washing becomes neutral, and eluting with 1.4% ammonia water followed by concentrating the eluate in vacuo.

The synthesis of beta-hydroxyalkyl-substituted compounds is conducted as follows. Thus, for example, 4-O-alpha- D-glucopyranosyl-moranoline is heated, with stirring, for several hours at 100°–110° C. with 3–8 equivalents of glycidyl phenyl ether in 10–20 times the amount of N,N-dimethylformamide or dimethyl sulfoxide. Purification of the resulting product may be conducted as follows. Thus, the crude product is treated with, for example, Dowex 50W×2 ($H^+$), then an equimolar amount of p-toluenesulfonic acid is added in an alcoholic solvent (e.g. methanol), the solvent is evaporated therefrom in vacuo, and the residue is recrystallized from alcoholic solvent (e.g. isopropanol) to give 4-O-alpha-D-glucopyranosyl-N-(2-hydroxy-3-phenoxypropyl)moranoline as the p-toluenesulfonate in pure form.

The ability of the compounds (I) of the present invention to inhibit blood sugar level increase was determined as follows:

MEASUREMENT OF ALPHA-GLUCOSIDASE INHIBITING ACTION IN VITRO

The activity of the test compounds in inhibiting sucrase and maltase in vitro using a crudely purified enzyme preparation (purified in accordance with a method of Takesue, 1969) obtained from rabbit small intestine mocosa was carried out as follows.

To 40 microliters of enzyme solution diluted with 0.4M phosphate buffer (pH 7.0) are added 20 microliters of a solution of a test compound in the same buffer and 140 microliters of a solution of a substrate (50 mM sucrose or 50 mM maltose) in the same buffer and the mixture is allowed to react at 37° C. for 30 minutes. The reaction is then stopped by adding 400 microliters of 3N barium hydroxide and 400 microliters of 5% zinc sulfate solution. The amount of the enzyme that is reacted is determined as the amount of glucose contained in 200 microliters of the supernatant liquid of the reaction solution by adding 3 ml of glucoseoxidase reagent (Bioehringer-Mannheim) followed by reacting at ambient temperature for 30 minutes and measuring the absorbance at 420 nm. The concentration of the compound that provides 50% inhibition ($IC_{50}$) of sucrase and maltase is calculated by expressing the values (as measured by the above method with five different concentrations) as an inhibitory rate (%) to the control. The result is given in Table 1.

TABLE 1

| Example No. | (1) Sucrase | (2) Maltase |
|---|---|---|
| 1 | 15.5 | 23.5** |
| 3 | 17.2* | 248.9* |
| 4 | 10.0 | 34.2 |
| 6 | 30.8 | 192.5 |
| 8 | 24.8* | 173.0* |
| 9 | 6.4 | 223.6 |
| 12 | 21.9** | 2.0** |
| 13 | 22.9 | 262.1* |
| 14 | 6.8 | 168.6 |
| 17 | 5.2* | 77.9* |
| 18 | 19.8 | 44.6 |
| 20 | 9.7 | 284.9 |
| 22 | 16.1 | 40.9 |
| 25 | 14.0 | 69.2* |

Unit: μg/ml.
The data are average of three measurements except for * which is an average of four measurements.
**is an inhibitory rate at 100 μg/ml.

It is apparent that the compounds of the present invention exhibit excellent inhibition of glucosidase activity.

INHIBITORY ACTION AGAINST INCREASE IN BLOOD GLUCOSE LEVEL IN RATS

SD-Strain rats (5 weeks age; male; each group comprising 4 to 5 rats) were fasted overnight and then given 1 ml/100 g body weight of aqueous solution of sucrose (2 g/10 ml) containing 30 mg test compound per os through a stomach tube.

Blood was taken from the tail vein immediately before the administration and at 30, 60, 90, 120 and 180 minutes thereafter and blood glucose levels were measured by a glucose oxidase method (using the assay kit prepared by Boehringer Mannheim).

Based on the values obtained above, a graph was drawn using time as the abscissa and blood glucose level as the ordinate and the area ($\Delta AUC$) under the time-blood glucose increase curve was determined.

A group of rats receiving only water and another group receiving only sucrose were designated as a basal group (group B) and a control group (group C), respectively. Then the inhibitory rate for an increase in $\Delta AUC$ 180 minutes after administration of the test compounds (group T) was calculated from the following expression.

Inhibitory Rate =

$$\frac{(\Delta AUC \text{ of Group C}) - (\Delta AUC \text{ of Group T})}{(\Delta AUC \text{ of Group C}) - (\Delta AUC \text{ of Group B})} \times 100$$

The result is given in Table 2.

TABLE 2

| | Example No. | | | | | | | | | | | | | | |
|---|---|---|---|---|---|---|---|---|---|---|---|---|---|---|---|
| | 1 | 3 | 5 | 6 | 8 | 9 | 12 | 13 | 14 | 17 | 18 | 19 | 20 | 22 | 25 |
| Inhibitory Rate(%) | 68.6 | 73.2 | 94.8 | 69.9 | 54.8 | 64.5 | 46.6 | 77.1 | 86.9 | 80.2 | 47.9 | 54.0 | 76.8 | 48.4 | 84.4 |

It is apparent that the compounds of the present invention inhibit blood glucose level increase in rats.

The toxicity of the compounds (I) was tested by giving the compound of Example 1 orally to mice (5 g/kg) but there were no deaths.

Compounds (I) of the invention are used to inhibit an increase in blood glucose in animals, including humans, and to treat animals, including humans, suffering from diabetes mellitus, by administering to the animal in need thereof an effective amount of the compound (I) of the invention, preferably in the form of a pharmaceutical composition comprising an effective amount of the compound (I) in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the daily dosage for humans will be from about 10 to about 2000 mg., preferably from about 100 to about 600 mg. In some instances, a sufficient therapeutic effect can be obtained at a lower dose, while in others a large dose will be required.

While the routes of administration of the compounds (I) of the invention include oral, parenteral (i.e., intramuscular, intraperitoneal and intravenous), topical and rectal, oral administration is particularly preferred.

The preferred pharmaceutical compositions are therefore those in a form suitable for oral administration, such as tablets and liquids.

The present invention is illustrated in terms of its preferred embodiments in the accompanying Examples.

EXAMPLE 1

4-O-alpha-D-Glucopyranosyl-N-(p-methylbenzyl)-moranoline

4-O-alpha-D-Glucopyranosylmoranoline (5 g) was dissolved in 50 ml of dimethylformamide. Anhydrous potassium carbonate (6.4 g) was added thereto. Then, with stirring, 7.1 g of alpha-bromo-p-xylene was added. The mixture was made to react at 100° C. for 5 hours and filtered.

After evaporating the solvent, the residue was dissolved in water and partitioned with chloroform. Aqueous layer was treated with a column of 50 ml of strongly acidic ion exchange resin (Dowex 50W×2 (H$^+$)), the column was well washed with water, eluted with 1N ammonia water, solvent was evaporated from the eluate in vacuo, the resulting powder (5.8 g) was dissolved in methanol, and 3.9 g of p-toluensulfonic acid monohydrate was added. The solution was concentrated in vacuo and, when crystals were separated out, the concentrating operation was stopped and ethanol was added so that crystals were fully separated out. The mixture was filtered and 7.2 g of crystals were obtained. They were dissolved in water, the solution was applied to a column of 30 ml of Diaion SA-11A and the column was well washed with water.

The solution which passed through and the washing were combined and the solvent was evaporated therefrom followed by drying to give 4.5 g of crystalline powder. M.p. 116°–119° C. $[\alpha]_D^{24} = +50.5°$ (c=0.94%, water).

Elem Anal for $C_{20}H_{31}N\ O_9 \cdot \frac{1}{2}H_2O$, Calculated (%) C: 54.79 H: 7.36 N: 3.19, Found (%) C: 54.92 H: 7.53 N: 3.31.

EXAMPLE 2

4-O-alpha-D-Glucopyranosyl-N-(4-methylcarbamoylbutyl)-moranoline p-toluenesulfonate The same operation as in Example 1 was conducted using N-methylcarbamoylbutyl bromide to give 5.0 g of the desired product, m.p. 125°–127° C. $[\alpha]_D^{24} = +47.7°$ (c=1.0%, water)

Elem Anal for $C_{25}H_{42}N_2O_{13}S$, Calculated (%) C: 49.17 H: 6.93 N: 4.59, Found (%) C: 48.73 H: 7.08 N: 4.66.

EXAMPLE 3

4-O-alpha-D-Glucopyranosyl-N-(3-methylcrotyl)-moranoline p-toluensulfonate.

4-O-alpha-D-Glucopyranosylmoranoline (1.00 g), 1.60 g of anhydrous potassium carbonate and 3.00 g of 1-bromo-3-methyl-2-butene were mixed with 15 ml of dimethyl sulfoxide, the mixture was stirred for 1 hour at ambient temperature, and heated with stirring at 100°–110° C. for 3 hours. After cooled, the mixture was filtered. The insoluble matter was washed with 10 ml of dimethyl sulfoxide and the washing was combined with the filtrate. To this was added 30 ml of water, the mixture was transferred to a separating funnel and washed 2 times with each 20 ml chloroform. The aqueous layer was passed through a column of 30 ml of strongly acidic ion exchanger (Dowex 50W×2 (H$^+$)), the column was washed with water until the washing became neutral, and eluted with 200 ml of 1.4% ammonia water. To the eluate was added small amount of antifoaming agent, the mixture was concentrated to dryness in vacuo, and 0.67 g of crude product was obtained.

This was dissolved in 5 ml of ethanol, 0.70 g of p-toluenesulfonic acid was dissolved therein, ethanol was evaporated in vacuo from the mixture, and the residue was dried and recrystalized from ethanol to give 0.23 g of colorless powder. M.p. 194°–196° C. $[\alpha]_D^{24} = +48.6°$ (c=1.144, water).

Elem Anal for $C_{17}H_{31}N\ O_9 \cdot C_7H_8O_3S$, Calculated (%) C: 50.69 H: 6.95 N: 2.48, Found (%) C: 50.26 H: 7.22 N: 2.48.

EXAMPLE 4

4-O-alpha-D-Glucopyranosyl-N-(p-bromobenzyl)-moranoline

4-O-alpha-D-Glucopyranosylmoranoline (5 g) and 6.4 g of anhydrous potassium carbonate were added to 50 ml of dimethylformamide, then 9.6 g of 4-bromobenzyl bromide was added, and the mixture was made to react at ambient temperature for 4 hours.

the precipitate was removed by filtration, the solvent was evaporated in vacuo, chloroform was added to the residue, the precipitate formed was collected by filtration, dissolved in water, and partitioned with ethyl acetate. Aqueous layer was treated with a column of 50 ml of strongly acidic ion exchange resin (Dowex 50W×2 (H$^+$)), the column was well washed with water, eluted with 1N ammonia water, the eluate was concentrated in vacuo, and the concentrate was treated with activated charcoal followed by evaporating to dryness. Recrystallization from methanol gave 4.7 g of crystals, m.p. 210°–212° C. $[\alpha]_D^{24} = +55.5°$ (c=1.0%, water).

Elem Anal for $C_{19}H_{28}N\ O_9Br$, Calculated (%) C: 46.16 H: 5.71 N: 2.83, Found (%) C: 46.03 H: 5.87 N: 2.88.

EXAMPLE 5

4-O-alpha-D-Glucopyranosyl-N-hexylmoranoline p-toluenesulfonate

A mixture of 1.00 g of 4-O-alpha-D-glucopyranosylmoranoline, 1.60 g of anhydrous potassium carbonate, 2.00 g of 1-bromohexane and 15 ml of dimethyl sulfoxide was stirred at ambient temperature for 1 hour, heated at 100°–110° C. with stirring for 3 hours, allowed to cooled, filtered, and the insoluble matter was washed with 5 ml of dimethyl sulfoxide. The filtrate was combined with the washing, 20 ml of water was added to the combined liquid, the mixture was transferred to a separating funnel, and washed twice with chloroform (20 ml each). The aqueous layer was applied to a column of 30 ml of strongly acidic ion exchange resin (Dowex 50W×2 (H$^+$)), the column was washed with water, eluted with 200 ml of 1.5% ammonia water, small amount of antifoaming agent was added to the eluate, and the mixture was concentrated in vacuo to dryness to give 0.42 g of pale brown substance.

This was dissolved in 5 ml of ethanol, 0.42 g of p-toluenesulfonic acid was added, and ethanol was evaporated from the mixture in vacuo. The residue was dissolved in 5 ml of ethanol, the solution was allowed to stand after addition of 3 ml of acetone, and the resulting precipitate was filtered to give 0.32 g of colorless powder. M.p. 194°–195° C. $[\alpha]_D^{24} = +55.6°$ (c=1.151, water).

Elem Anal for $C_{18}H_{35}N\ O_9\cdot C_7H_8O_3S$, Calculated (%) C: 51.62 H: 7.45 N: 2.41, Found (%) C: 51.91 H: 7.40 N: 2.39.

EXAMPLE 6

4-O-alpha-D-Glucopyranosyl-N-(beta-phenylethyl)-moranoline

To 50 ml of dimethylformamide were added 5 g of 4-O-alpha-D-glucopyranosylmoranoline and 6.4 g of anhydrous potassium carbonate. To this was added 7.1 g of beta-phenylethyl bromide with stirring and the mixture was made to react at 100° C. for 5 hours.

The reaction solution was filtered to remove the precipitate, the filtrate was concentrated in vacuo, then chloroform was added thereto, the precipitate obtained was collected by filtration, dissolved in water, and the solution was treated with a column of 60 ml of strongly acidic ion exchanger (Dowex 50W×2 (H+)). The column was well washed with water followed by eluting with 1N ammonia water.

The solvent was removed in vacuo from the eluate and the residue was treated with a column of 40 g of silica gel. The column was developed with an eluting solution of chloroformmethanol (1:1) to collect a fraction containing the desired product which was evaporated to dryness in vacuo to give 3.7 g of powder. No clear melting point but it started to melt at 87°–89° C. and finished the melting at 100°–106° C. $[\alpha]_D^{24} = +71.2°$ (c=0.98, water).

Elem Anal for $C_{20}H_{31}N\ O_9$, Calculated (%) C: 55.94 H: 7.28 N: 3.26, Found (%) C: 55.64 H: 7.25 N: 3.55.

EXAMPLE 7

4-O-alpha-D-Glucopyranosyl-N-(beta-cyclohexylethyl)moranoline

The same operation as in Example 6 was conducted with an exception of the use of beta-cyclohexylethyl bromide to give 4.0 g of the product. M.p. 88°–90° C. $[\alpha]_D^{24} = +65.3°$ (c=1.00, water).

Elem Anal for $C_{20}H_{37}N\ O_9$, Calculated (%) C: 55.16 H: 8.56 N: 3.22, Found (%) C: 54.83 H: 8.78 N: 3.30.

EXAMPLE 8

4-O-alpha-D-Glucopyranosyl-N-(p-methoxybenzyl)-moranoline

A mixture of 2.00 g of 4-O-alpha-D-glucopyranosylmoranoline, 4.24 g of anhydrous potassium carbonate, 5.50 g of p-methoxybenzyl chloride and 20 ml of dimethylformamide was stirred at 60° C. for 1 hour and heated with stirring at 100°–105° C. for 6 hours. The reaction solution was filtered when it is still hot and the insoluble matter was washed with small amount of dimethylformamide. The filtrate was combined with the washing and dimethylformamide was removed in vacuo therefrom. The residue was washed twice with each 20 ml ether. The ether-insoluble matter was dissolved in water, treated with a column of 50 ml of strongly acidic ion exchange resin (Dowex 50W×2 (H+)), the column was washed with water, eluted with 200 ml of 1.5% ammonia water, small amount of antifoaming agent was added to the eluate, and the mixture was evaporated to dryness in vacuo to give 1.18 g of hygroscopic pale yellow powder. This was dissolved in 50 ml of methanol, the solution was stirred 2 hours at ambient temperature with activated charcoal, then the charcoal was removed, 2.00 g of p-toluenesulfonic acid was dissolved in the filtrate, methanol was evaporated in vacuo therefrom, and the residue was crystallized from isopropanol to give 1.40 g of colorless crystals, m.p. 167°–169° C. (decomp.). $[\alpha]_D^{24} = +49.49°$ (c=1.180, water).

Elem Anal for $C_{20}H_{31}N\ O_{10}\cdot C_7H_8O_3S$, Calculated (%) C: 52.50 H: 6.36 N: 2.72, Found (%) C: 52.03 H: 6.49 N: 2.32.

EXAMPLE 9

4-O-alpha-D-Glucopyranosyl-N-(beta-phenoxyethyl)-moranoline

To 50 ml of dimethylformamide were added 5 g of 4-O-alpha-D-glucopyranosylmoranoline and 6.4 g of anhydrous potassium carbonate. beta-Bromophenethol (7.7 g) was added thereto with stirring and the mixture was made to react at 110° C. for 3 hours.

The precipitate was removed by filtering the reaction solution. The filtrate was concentrated in vacuo, chloroform was added to the concentrate, the resulting precipitate was collected by filtration, dried with air, dissolved in water, and the solution was treated with a column of 100 ml of Dowex 50W×2 (H+)). The column was well washed with water and eluted with 1N ammonia water.

The solvent was evaporated in vacuo, the residue was dissolved in ethanol, the resulting very small amount of insoluble matter was removed by filtration, the filtrate evaporated to remove ethanol in vacuo, and the residue was dried to give 4.3 g of the crystalline powder, m.p. 92°–94° C., $[\alpha]_D^{24} = +65.9°$ (c=1%, water).

Elem Anal for $C_{20}H_{31}N\ O_{10}$, Calculated (%) C: 53.93 H: 7.01 N: 3.14, Found (%) C: 53.43 H: 7.07 N: 3.05.

EXAMPLE 10

4-O-alpha-D-Glucopyranosyl-N-(3-methyl-3-thienylally)moranoline

Grignard reagent prepared from 13 g of vinyl bromide was made to react with 12.5 g of alpha-acetylthiophene to give 14.8 g of yellow oily carbinol. Tetrabromomethane (30 g) was added to it in 100 ml of acetonitrile and 25 g of triphenylphosphine was added little by little thereto with ice cooling and stirring and the mixture was stirred at 15°–20° C. for 2 hours. This was evaporated to dryness at not higher than 30° C. in vacuo and the residue was extracted with ether. Ether was evaporated therefrom at not higher than 30° C. and the residue was made to react at 50°–60° C. for 1 hour with 6 g of 4-O-alpha-D-glucopyranosylmoranoline and 12 g sodium bicarbonate in ethyleneglycol. Then the mixture was processed the same as in Example 9 to give 0.7 g of the product, m.p. 141°–143° C. $[\alpha]_D^{24} = +30.8°$ (c=1%, water).

EXAMPLE 11

4-O-alpha-D-Glucopyranosyl-N-(2-oxobutyl)moranoline

The same operation as in Example 9 was conducted using 1-bromo-2-butanone to give 2.1 g of the desired product, m.p. 101°–105° C. $[\alpha]_D^{24} = +73.3°$ (c=1%, water).

EXAMPLE 12

4-O-alpha-D-Glucopyranosyl-N-(4-carboxybenzyl)-moranoline p-toluenesulfonate To 50 ml of dimethylforamide were added 4.5 g of 4-O-alpha-D-glucopyranosylmoranoline and 8.3 g of anhydrous potassium carbonate. To this was added 5 g of p-(bromomethyl)-benzoic acid with stirring and the mixture was made to react at 110° C. for 5 hours.

The reaction solution was filtered to remove the precipitate, the solvent was evaporated in vacuo from the filtrate, to the residue was added chloroform, the resulting insoluble matter was collected by decantation, dried in vacuo, then dissolved in water, the solution was passed through a column of 100 ml of Dowex 50W×2 (H+) and the column was well washed with water and eluted with 1N ammonia water.

The solvent was evaporated in vacuo, the residue was dissolved in small amount of water, and acetone was added to the solution. To this was added 3.0 g of p-toluenesulfonic acid monohydrate, the mixture was allowed to stand at 5° C., and the resulting precipitate was collected by filtration, washed with cold ethanol and dried to give 3.6 g of crystals. M.p. 251°–253° C., $[\alpha]_D^{24} +54.4°$ (c=1%, water).

Elem Anal for $C_{27}H_{37}N\ O_{14}S$, Calculated (%) C: 54.09 H: 6.22 N: 2.34, Found (%) C: 53.59 H: 6.27 N: 2.24.

EXAMPLE 13

4-O-alpha-D-Glucopyranosyl-N-allylmoranoline p-toluenesulfonate

A mixture of 2.00 g of 4-O-alpha-D-glucopyranosyl-moranoline, 4.24 g of anhydrous potassium carbonate, 10.0 g of allyl bromide and 20 ml of dimethylformamide was stirred at 60° C. for 1 hour and heated with stirring at 90°–100° C. for 6 hours. After cooling, this was filtered to remove the insoluble matter and the filtrate was evaporated to dryness in vacuo. The residue was dissolved in 50 ml of water, the solution was passed through a column of 50 ml of Dowex 50W×2 (H+), the column was washed with water, eluted with 30 ml of 1.4% ammonia water, small amount of antifoaming agent was added to the eluate, and the mixture was evaporated to dryness in vacuo to give 1.18 g of hygroscopic pale yellow powder. This was dissolved in 50 ml of methanol, the solution was stirred at ambient temperature for 2 hours with activated charcoal, then the charcoal was removed, 1.0 g of p-toluenesulfonic acid was dissolved in the filtrate, and methanol was evaporated from the solution to dryness in vacuo. The product was crystallized from isopropanol to give 0.74 g of colorless granules. M.p. 194°–195° C. $[\alpha]_D^{24} = +58.52°$ (c=1.073, water).

Elem Anal for $C_{15}H_{27}N\ O_9.C_7H_8O_3S$, Calculated (%) C: 49.15 H: 6.56 N: 2.61, Found (%) C: 49.01 H: 6.47 N: 2.40.

EXAMPLE 14

4-O-alpha-D-Glucopyranosyl-N-(4-phenoxybutyl)-moranoline.

To 50 ml of dimethylformamide were added 5 g of 4-O-alpha-D-glucopyranosylmoranoline and 6.4 g of anhydrous potassium carbonate. To this was added 8.8 g of 4-phenoxybutyl bromide and the mixture was made to react at 110° C. for 5 hours. The reaction solution was filtered to remove the precipitate and the solvent was evaporated in vacuo therefrom. To this was added chloroform, the resulting precipitate was collected by filtration dissolved in water, and the solution was partitioned with chloroform. The aqueous layer was evaporated to dryness in vacuo and ethanol was added to the residue. Small amount of insoluble matters was removed by filtration, then ethanol was evaporated therefrom, the residue was dissolved in water, and the solution was passed through a column of 100 ml of Dowex 50W×2 (H+). The column was well washed with water, eluted with 1N ammonia water, the fractions were collected the solvent was evaporated in vacuo therefrom, and dried to give 5.5 g of crystalline powder, m.p. 85°–87° C. $[\alpha]_D^{24} = +60.1°$ (c=1%, water).

Elem Anal for $C_{22}H_{35}N\ O_{10}$, Calculated (%) C: 55.80 H: 7.45 N: 2.96, Found (%) C: 55.10 H: 7.40 N: 3.04.

EXAMPLE 15

4-O-alpha-D-Glucopyranosyl-N-(beta-phenylthioethyl)moranoline

The same operation as in Example 14 was conducted using 2-phenylthioethyl bromide to give 3.3 g of desired product, m.p. 96°–98° C. $[\alpha]_D^{24} = +70.1°$ (c=1%, water).

Elem Anal for $C_{20}H_{31}N\ O_9S$, Calculated (%) C: 52.05 H: 6.77 N: 3.04, Found (%) C: 51.56 H: 6.99 N: 3.21.

EXAMPLE 16

4-O-alpha-D-Glucopyranosyl-N-[beta-(4-ethoxycarbonylphenoxy)ethyl]moranoline

The same operation as in Example 14 was conducted using beta(4-ethoxycarbonylphenoxy)ethyl bromide to give 3.8 g of the desired product, m.p. 123°–125° C. $[\alpha]_D^{24} = +60.1°$ (c=1%, water).

Elem Anal for $C_{23}H_{35}N\ O_{12}$, Calculated (%) C: 53.38 H: 6.82 N: 2.71, Found (%) C: 53.01 H: 6.91 N: 2.84.

EXAMPLE 17

4-O-alpha-D-Glucopyranosyl-N-nonylmoranoline hydrate

A mixture of 1.00 g of 4-O-alpha-D-glucopyranosyl-moranoline, 2.00 g of anhydrous potassium carbonate, 2.00 g of 1-bromononane, and 15 ml of dimethyl sulfoxide was stirred at ambient temperature for 1 hour and heated with stirring at 100°–110° C. for 3 hours. After the reaction, the mixture was filtered to remove insoluble matters, the filtrate was evaporated in vacuo to remove dimethyl sulfoxide, the residue was washed twice with 10 ml of ether each, and the substance insoluble in ether was dissolved in 20 ml of water. This solution was passed through a column of 30 ml of Dowex 50W×2 (H+), the column was washed with water, eluted with 200 ml of 1.4% ammonia water, to the eluate was added small amount of antifoaming agent, and the mixture was evaporated in vacuo to dryness to give 0.30 g of colorless powder. Purification was conducted by a high performance liquid chromatography (Nucleosil 5 NH2; column size: 10×105 mm; acetonitrile-water=7:3; 1.0 ml/min, RI detector) to give 0.10 g of the product. M.p. 112°–113° C. $[\alpha]_D^{24} = +58.64°$ (c=0.665, water.).

Elem Anal for $C_{21}H_{41}N\ O_9.H_2O$, Calculated (%) C: 53.72 H: 9.23 N: 2.98, Found (%) C: 54.07 H: 9.16 N: 3.01.

EXAMPLE 18

4-O-alpha-D-Glucopyranosyl-N-(4-methoxycarbonylbutyl)moranoline p-toluenesulfonate To 50 ml of dimethylformamide were added 5 g of 4-O-alpha-D-glucopyranosylmoranoline and 6.4 g of anhydrous potassium carbonate. To this was added 7.5 g of methyl 5-bromovalerate and the mixture was made to react at 110° C. for 3 hours. The reaction solution was filtered to remove the precipitate and the solvent was evaporated in vacuo therefrom. To the residue was added chloroform, the mixture was decantated to remove chloroform-soluble matters, the precipitate thus obtained was dried in vacuo, dissolved in water, and the solution was passed through a column of 100 ml of Dowex 50W×2 (H+). The column was well washed with water, eluted with 1N ammonia water, the fractions were collected, the solvent was evaporated therfrom in vacuo, and the residue was dried. To this was added 100 ml of ethanol, then small amount of methanol was further added, and to the resulting solution was added 3.8 g of p-toluenesulfonic acid (monohydrate). The mixture was concentrated, filtered to collect the crystals, and the crystals were washed with ethanol and dried to give 5.9 g of crystalline powder, m.p. 114°-116° C. $[\alpha]_D^{24} = +45.3°$ (c=1%, water).

Elem Anal for $C_{25}H_{41}N\ O_{14}S$, Calculated (%) C: 49.09 H: 6.76 N: 2.29. Found (%) C: 48.39 H: 7.04 N: 2.05.

EXAMPLE 19

4-O-alpha-D-Glucopyranosyl-N-phenethylmoranoline p-toluenesulfonate

A mixture of 2.00 g of 4-O-alpha-D-glucopyranosylmoranoline, 3.39 g of anhydrous potassium carbonate, 5.69 g of phenethyl bromide, and 20 ml of dimethylformamide was stirred at 60° C. for 1 hour and then heated with stirring at 100°-110° C. for 6 hours. The reaction solution was filtered when it was still hot, the insoluble matter was washed with small amount of dimethylformamide, the washing was combined with the filtrate, and dimethylformamide was evaporated in vacuo therefrom. The residue was washed twice with 20 ml of ether each. The ether-insoluble matters were dissolved in water, the solution was passed through a column of 50 ml of Dowex 50W×2 (H+), the column was washed with water, and eluted with 300 ml of 1.4% ammonia water. Small amount of antifoaming agent was added to the eluate and the mixture was evaporaed to dryness in vacuo to give 0.8 g of pale yellow powder. This was dissolved in 20 ml of methanol, the solution was stirred at ambient temperature for 2 hours with activated charcoal, the charcoal was removed by filtration, 0.80 g of p-toluenesulfonic acid was dissolved in the filtrate, methanol was evaporated in vacuo therefrom, and the residue was dried. This was recrystallized from isopropanol twice to give 0.42 g of colorless crystals. M.p. 129°-130° C. $[\alpha]_D^{24} = +50.75°$ (c=0.930, water)

Elem Anal for $C_{20}H_{31}N\ O_9.C_7H_8O_3S.H_2O$, Calculated (%) C: 52.33 H: 6.67 N: 2.26, Found (%) C: 52.33 H: 6.87 N: 2.11.

EXAMPLE 20

4-O-alpha-D-Glucopyranosyl-N-cinnamylmoranoline p-toluenesulfonate

To 50 ml of dimethylformamide were added 5 g of 4-O-alpha-D-glucopyranosylmoranoline and 6.4 g of anhydrous potassium carbonate. To this was added 7.6 g of cinnamyl bromide and the mixture was made to react at ambient temperature for 1 hour. The reaction solution was filtered to remove the precipitate and the solvent was removed from the filtrate in vacuo. Water was added to the residue, the mixture was well stirred, and partitioned by addition of chloroform thereto. The aqueous layer was passed through a column of 100 ml of Dowex 50W×22 (H+). The column was well washed with water and eluted with 1N ammonia water. The solvent was evaporated from the eluate. The residue was dissolved in methanol and, after addition of 2.5 g of p-toluenesulfonic acid thereto, the mixture was concentrated until crystals separated out. The resulting crystals were collected by filtration, washed with ethanol, and dried to give 2.0 g of crystalline powder, m.p. 212°-214° C. $[\alpha]_D^{24} = +35.2°$ (c=1%, water).

Elem Anal for $C_{28}H_{39}N\ O_{12}S$, Calculated (%) C: 54.80 H: 6.41 N: 2.28, Found (%) C: 54.64 H: 6.51 N: 2.09.

EXAMPLE 21

4-O-alpha-D-Glucopyranosyl-N-[p-(3-hydroxypropenyl)-cinnamyl]moranoline hydrochloride The same operation as in Example 20 was conducted using p-(3-hydroxypropenyl)-cinnamyl bromide to give 0.5 g of the desired product, m.p. 220°-225° C. $[\alpha]_D^{24} = +26.1°$ (c=1%, water).

Elem Anal for $C_{24}H_{35}N\ O_{10}.HCl$, Calculated (%) C: 53.98 H: 6.80 N: 2.62, Found (%) C: 53.41 H: 7.11 N: 2.89.

EXAMPLE 22

4-O-alpha-D-Glucopyranosyl-N-(2-hydroxy-3-phenoxypropyl)moranoline p-toluenesulfonate hydrate A mixture of 2.00 g of 4-O-alpha-D-glucopyranosylmoranoline, 5.54 g of glycidyl phenyl ether and 30 ml of dimethylformamide was heated with stirring at 100°-110° C. for 7.5 hours. Dimethylformamide was evaporated therefrom in vacuo. The residue was washed twice with 10 ml of ether each. The ether-insoluble matters were dissolved in 30 ml of water, the solution was passed through a column of 30 ml of Dowex 50W×2 (H+), the column was washed with water until the washing became neutral, and eluted with 200 ml of 1.4% ammonia water. Small amount of antifoaming agent was added to the eluate and the mixture was concentrated to dryness in vacuo to give 0.5 g of residue. This was dissolved in 20 ml of methanol, 0.5 g of p-toluenesulfonic acid was dissolved therein, methanol was evaporated in vacuo therefrom, and the residue was dried, washed with ether, and crystallized from isopropanol to give 0.3 g of colorless cubes, m.p. 104° C. $[\alpha]_D^{24} = +49.61°$ (c=1.032, water).

Elem Anal for $C_{21}H_{33}N\ O_{11}.C_7H_8O_3S.H_2O$, Calculated (%) C: 50.52 H: 6.51 N: 2.10, Found (%) C: 50.58 H: 6.46 N: 1.96.

EXAMPLE 23

4-O-alpha-D-Glucopyranosyl-N-(beta-ethoxy)ethylmoranoline p-toluenesulfonate

Ten grams of hepta-O-benzyl derivative of 4-O-alpha-D-glucopyranosyl-N-(beta-hydroxy)ethylmoranoline was made to react with 20 ml of thionyl chloride at 80° C. for 3 hours, the mixture was evaporated to dryness in vacuo, the residue was added to 200 ml of ethanol in which 2 g of sodium was dissolved, and the mixture was made to react at 50° C. for 5 hours. Ethanol was removed therefrom, the residue was dissolved in benzene, and washed with water. The resulting reaction product was purified with a column of silica gel using chloroform-ethyl acetate (5:1) as a developer. The resulting product (9 g) was dissolved in ethanol and subjected to catalytic hydrogenation using palladium as a catalyst. The catalyst was filtered off, the filtrate was evaporated, the residue, was dissolved in water, and the solution was passed through a column of 100 ml of Dowex 50W×2 (H+). The column was well washed with water and eluted with 1N ammonia water. The eluate was evaporated in vacuo the residue was dissolved in ethanol, 2.5 g of p-toluenesulfonic acid (monohydrate) was added, and the mixture was concentrated until crystals separated out. The resulting crystals were collected by filtration, washed with ethanol, and dried to give 2.3 g of crystalline powder, m.p. 117°–119° C. $[\alpha]_D^{24} = +85.6°$ (c=1%, water).

EXAMPLE 24

4-O-alpha-D-glucopyranosyl-N-(beta-diethylaminoethyl)moranoline p-toluenesulfonate.

Ten grams of hepta-O-benzyl derivative of 4-O-alpha-D-glucopyranosyl-N-(beta-hydroxyethyl)-moranoline was made into a chloro compound by the same way as in Example 23, then made to react with diethylamine in ether, and the mixture was evaporated to dryness followed by the same treatment as in Example 23 to give 1.8 g of desired product. M.p. 161°–163° C. $[\alpha]_D^{24} = +80.2°$ (c=1%, water).

EXAMPLE 25

4-O-alpha-D-Glucopyranosyl-N-(p-methylbenzyl)-moranoline p-toluenesulfonate

A mixture of 2.00 g of 4-O-alpha-D-glucopyranosyl-moranoline, 4.24 g of anhydrous potassium carbonate, 3.61 g of p-methylbenzyl bromide and 20 ml of dimethylformamide was stirred at 60° C. for 1 hour and heated at 100°–110° C. with stirring. After cooling, the mixture was filtered to remove insoluble matters, and the filtrate was evaporated to dryness in vacuo.

The residue was washed twice with each 10 ml ether, the ether-insoluble matters were dissolved in 50 ml of water, the solution was passed through a column of 50 ml of Dowex 50W×2 (H+), the column was washed with water, and eluted with 300 ml of 1.4% ammonia water. Small amount of antifoaming agent was added to the eluate and the mixture was evaporated to dryness in vacuo to give 1.18 g of hygroscopic pale yellow powder. This was dissolved in 50 ml of methanol, the solution was stirred with activated charcaol at ambient temperature for 2 hours, the charcoal was removed, 2.00 g of p-toluenesulfonic acid was dissolved in the solution, methanol was evaporated therefrom in vacuo, and the residue was dried followed by crystallizing from isopropanol to give 1.46 g of colorless crystals. M.p. 158°–160° C. $[\alpha]_D^{24} = +49.11°$ (c=1.124, water).

Elem Anal for $C_{20}H_{31}N\ O_9 \cdot C_7H_8O_3S$, Calculated (%) C: 53.90 H: 6.53 N: 2.33, Found (%) C: 53.88 H: 6.31 N: 2.09.

EXAMPLE 26

4-O-alpha-D-Glucopyranosyl-N-pentadecylmoranoline p-toluenesulfonate

A mixture of 2.00 g of 4-O-alpha-D-glucopyranosyl-moranoline, 3.40 g of anhydrous potassium carbonate, 3.3 g of 1-bromopentadecane and 20 ml of dimethylformamide was stirred at 60°–70° C. for 1 hour and heated with stirring at 100°–110° C. for 3 hours. The mixture was filtered to remove the insoluble matters and the filtrate was evaporated to dryness in vacuo. The residue was washed twice with each 10 ml of ether. To the ether-insoluble matter was added 30 ml of water, the mixture was warmed to make it dissolved, and allowed to cool. Gel-like substances separated out therefrom were collected by filtration, dissolved in 30 ml of methanol, activated charcoal was added thereto, the mixture was stirred 2 hours at ambient temperature, the charcoal was removed, 0.80 g of p-toluenesulfonic acid was added to the solution, and the mixture was evaporated to dryness in vacuo. The residue was crystallized from isopropanol to give 0.40 g of desired product, m.p. 173°–175° C. $[\alpha]_D^{24} = +43.19°$ (c=1.102, methanol).

Elem Anal for $C_{27}H_{53}N\ O_9 \cdot C_7H_8O_3S$, Calculated (%) C: 57.69 H: 8.68 N: 1.98, Found (%) C: 57.22 H: 8.74 N: 1.94.

We claim:

1. A compound of formula (I)

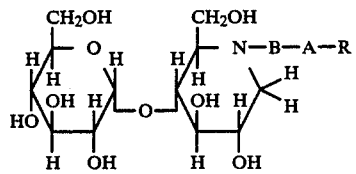

wherein:

B is a divalent cyclic or acyclic, saturated or unsaturated aliphatic hydrocarbon group containing up to about 15 carbon atoms, unsubstituted or substituted by at least one substituent selected from the group consisting of halogen, hydroxyl, mercapto, amino, phenyl, naphthyl or heterocyclyl or substituted phenyl, naphthyl or heterocyclyl, said substituted phenyl, naphthyl and heterocyclyl being substituted by at least one substituent selected from the group consisting of monovalent aliphatic hydrocarbon containing from about 1 to about 15 carbon atoms, halogen, hydroxy, mercapto, amino, carboxyl, alkoxycarbonyl containing from about 1 to about 15 carbon atoms in the alkoxy moiety, phenyl, naphthyl and heterocyclyl, each said heterocyclyl having from 5 to 12 ring members and containing 1, 2 or 3 heteroatoms selected from the group consisting of nitrogen, oxygen and sulfur;

A is a linking group selected from the group consisting of —O—, —S—, —N(H)—, —N(R¹)—, wherein R¹ is alkyl of 1 to 6 carbon atoms, —C(O)O—, —C(O)NH— and —C(O)— or A is a direct bond; and R is a monovalent cyclic or acyclic, saturated or unsaturated hydrocarbon group containing up to about 15 carbon atoms, unsubstituted or substituted by at least one substituent selected from the group consisting of halogen, hydroxyl, mercapto, amino, phenyl, naphthyl or heterocyclyl, or substituted phenyl, naphthyl or heterocyclyl, or R is phenyl, naphthyl or heterocyclyl or substituted phenyl, naphthyl or heterocyclyl, said substituted phenyl, naphthyl and heterocyclyl being substituted by at least one substituent selected from the group consisting of monovalent aliphatic hydrocarbon containing from about 1 to about 15 carbon atoms, alkoxy of from 1 to 4 carbon atoms in the alkyl moiety, hydroxypropenyl, halogen, hydroxy, mercapto, amino, carboxyl, alkoxycarbonyl containing from about 1 to about 15 carbon atoms in the alkoxy moiety, phenyl, naphthyl and heterocyclyl, each said heterocyclyl having 5 to 12 ring members and containing 1, 2 or 3 heteroatoms selected from the group consisting of nitrogen, oxygen and sulfur; provided that B—A—R may not represent hydrogen, lower alkyl or a monovalent cyclic or acyclic group having at least one hydroxy group.

2. The compound according to claim 1, wherein B is alkylene of from about 1 to about 15 carbon atoms, alkenylyl or alkynylyl of from about 2 to about 15 carbon atoms, or cycloalkylene, cycloalkenylyl or cycloalkynylyl of from about 3 to about 10 carbon atoms unsubstituted or substituted by at least one said substituent.

3. The compound according to claim 2, wherein R is alkyl of from about 1 to about 6 carbon atoms, alkenyl of from about 2 to about 6 carbon atoms, cycloalkyl of from 3 to 7 carbon atoms, thienyl, phenyl or phenyl substituted by alkyl of from about 1 to about 6 carbon atoms, alkoxy of from 1 to 4 carbon atoms in the alkyl moiety, hydroxypropenyl, halogen, hydroxy, carboxyl or alkoxycarbonyl of from about 1 to 6 carbon atoms in the alkoxy moiety.

4. The compound according to claim 3 wherein R is alkyl of from about 1 to about 6 carbon atoms, alkenyl of from about 2 to about 6 carbon atoms or phenyl.

5. The compound according to claim 3, wherein A is a direct bond, —C(O)—, —(O), —C(O)O—, —C(O)NH— or —N(R¹), wherein R¹ is alkyl of from about 1 to about 6 carbon atoms.

6. The compound according to claim 3, wherein B is alkylene of from about 1 to about 6 carbon atoms or alkenylyl or alkynylyl of from about 2 to about 6 carbon atoms, unsubstituted or substituted by halogen, hydroxy, mercapto, amino, phenyl or naphthyl.

7. A pharmaceutical composition for inhibiting an increase in glucose in animals, including humans, which comprises a therapeutically effective amount of a compound according to claim 1 in combination with a pharmaceutically acceptable diluent or carrier.

8. A method for inhibiting an increase in glucose in animals, including humans, which comprises administering to an animal in need thereof a therapeutically effective amount of a compound according to claim 1.

9. A pharmaceutical composition for treating animals, including humans, suffering from diabetes mellitus, which comprises a therapeutically effective amount of a compound according to claim 1 in combination with a pharmaceutically acceptable diluent or carrier.

10. A method for treating animals, including humans, suffering from diabetes mellitus, which comprises administering to the sufferer a therapeutically effective amount of a compound according to claim 1 in combination with a pharmaceutically acceptable diluent or carrier.

11. A compound of formula (I)

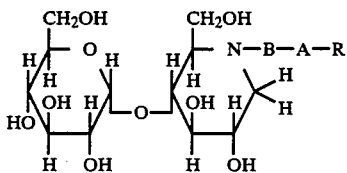

wherein A is a direct bond, B is alkenylyl of from about 2 to about 6 carbon atoms and R is alkyl of from about 1 to about 6 carbon atoms or A is a direct bond, B is alkylene of from about 1 to about 6 carbon atoms and R is alkenyl of from about 2 to about 6 carbon atoms.

12. The compound according to claim 11 which is 4-O-alpha-D-glucopyranosyl-N-(3-methylcrotyl)-moranoline or a pharmaceutically acceptable salt thereof.

13. A pharmaceutical composition for inhibiting an increase in glucose in animals, including humans, which comprises a therapeutically effective amount of a compound according to claim 11 in combination with a pharmaceutically acceptable diluent or carrier.

14. A method for inhibiting an increase in glucose in animals, including humans, which comprises administering to an animal in need thereof a therapeutically effective amount of a compound according to claim 11.

15. A pharmaceutical composition for treating animals, including humans, suffering from diabetes mellitus, which comprises a therapeutically effective amount of a compound according to claim 11 in combination with a pharmaceutically acceptable diluent or carrier.

16. A method for treating animals, including humans suffering from diabetes mellitus, which comprises administering to the sufferer a therapeutically effective amount of a compound according to claim 11 in combination with a pharmaceutically acceptable diluent or carrier.

17. A compound of formula I

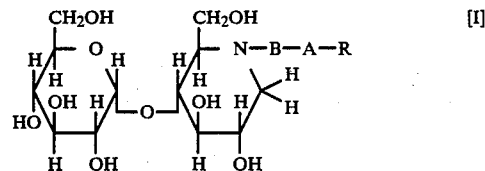

wherein B is alkylene of from about 1 to about 6 carbon atoms, A is —O— and R is phenyl.

18. The compound according to claim 17 which is 4-O-alpha-D-glucopyranosyl-N-(4-phenoxybutyl)-moranoline or a pharmaceutically acceptable salt thereof.

19. A pharmaceutical composition for inhibiting an increase in glucose in animals, including humans, which comprises a therapeutically effective amount of a compound according to claim 17 in combination with a pharmaceutically acceptable diluent or carrier.

20. A method for inhibiting an increase in glucose in animals, including humans, which comprises administering to an animal in need thereof a therapeutically effective amount of a compound according to claim 17.

21. A pharmaceutical composition for treating animals, including humans, suffering from diabetes mellitus, which comprises a therapeutically effective amount of a compound according to claim 17 in combination with a pharmaceutically acceptable diluent or carrier.

22. A method for treating animals, including humans suffering from diabetes mellitus, which comprises administering to the sufferer a therapeutically effective amount of a compound according to claim 17 in combination with a pharmaceutically acceptable diluent or carrier.

23. A compound of formula (I)

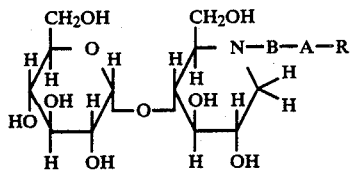 [I]

wherein B is alkylene of from about 1 to about 15 carbon atoms or alkenylyl or alkynylyl of from about 2 to about 15 carbon atoms, unsubstituted or substituted by halogen, hydroxy, mercapto, amino, phenyl or naphthyl;

A is a linking group selected from the group consisting of —O—, —S—, —N(H)—, —N($R^1$)—, wherein $R^1$ is alkyl of from 1 to 6 carbon atoms, —C(O)O—, —C(O)NH— and —C(O)— or A is a direct bond; and R is alkyl of from about 1 to about 6 carbon atoms, alkenyl of from about 2 to about 6 carbon atoms, cycloalkyl of from 3 to 7 carbon atoms, thienyl, phenyl or phenyl substituted by alkyl of from about 1 to about 6 carbon atoms, alkoxy of from 1 to 4 carbon atoms in the alkyl moiety, hydroxypropenyl, halogen, hydroxy, carboxyl or alkoxycarbonyl of from about 1 to about 6 carbon atoms in the alkoxy moiety; provided that B—A—R may not represent hydrogen, lower alkyl or a monovalent cyclic or acyclic group having at least one hydroxy group.

* * * * *